(12) United States Patent
Køhler et al.

(10) Patent No.: US 6,881,430 B2
(45) Date of Patent: Apr. 19, 2005

(54) FOOD COLORING SUBSTANCES AND METHOD FOR THEIR PREPARATION

(75) Inventors: Klaus Køhler, Frederiksberg C (DK); Martin Kensø, Hvidovre (DK); Claus Søndergaard, Roskilde (DK); Bjørn Madsen, Helsingør (DK); Søren Jan Jacobsen, Copenhagen S (DK)

(73) Assignee: Chr. Hansen A/S, Horsholm (DK)

( * ) Notice: Subject to any disclaimer, the term of this patent is extended or adjusted under 35 U.S.C. 154(b) by 151 days.

(21) Appl. No.: 10/205,533

(22) Filed: Jul. 26, 2002

(65) Prior Publication Data

US 2003/0082281 A1 May 1, 2003

Related U.S. Application Data

(60) Provisional application No. 60/308,108, filed on Jul. 30, 2001.

(30) Foreign Application Priority Data

Jul. 26, 2001  (EP) ............................................ 01202857

(51) Int. Cl.$^7$ ............................................... A23L 1/27
(52) U.S. Cl. ........................ 426/250; 426/262; 426/540
(58) Field of Search ................................ 426/250, 262, 426/540

(56) References Cited

U.S. PATENT DOCUMENTS

| 833,602 A | 10/1906 | Immerheiser et al. |
|---|---|---|
| 2,053,208 A | 9/1936 | Curtis et al. |
| 3,909,284 A | 9/1975 | Woznicki et al. |
| 4,475,919 A | 10/1984 | Woznicki et al. |

FOREIGN PATENT DOCUMENTS

| EP | 0025637 | 3/1981 |
|---|---|---|
| EP | 0 873 680 A1 | 10/1998 |
| JP | 63243167 | 11/1998 |
| WO | WO 97/26803 | 7/1997 |

OTHER PUBLICATIONS

Sam Asen et al.; Effect of Aluminum on Absorption Spectra of the Anthocyanin and Flavonols from Sepals of *Hydrangea macrophylla* var. *merveille*; U.S. Dept. of Agriculture; pp. 478–481; Proc. Am. Soc. Hort. Sci., vol. 70, 1957.

Warren E. Blumenthal; A Review of the Literature on Color Lakes; American Dyestuff Reporter, vol. 35, No. 23; pp. 529–538; 543–545; Nov. 1946.

E.M. Chenery; The Problem of the Blue Hydrangea; Journal of the Royal Agricultural Society, London; pp 304–305; 308–320. (1937).

Von Dr. O. Grube et al.; Der Farbstoff des Rotkohls als Indicator im pH–Bereich 8, 5—10; Chemiker–Zeitung; p. 34, (1943), Titled translated: "The pigment of red cabbage as an indication in the pH range 8, 5—10."

Leonard Jurd et al.; The Formation of Metal and "Co–Pigment" Complexes of Cyanidin 3–Glucoside; Phytochemistry, vol. 5; pp. 1263–1271; 1996.

Susumu Maekawa et al.; Effect of Aluminum Ions on the Bluing of Petal Color in Cut Chinese Bellflower, *Platycodon grandiflorum*; Plant & Cell Physiol., 24(4) pp. 759–764; 1983.

G.M. Sapers; Deodorization of a Colorant Prepared from Red Cabbage; Journal of Food Science, vol. 47; pp. 972–976; 1982.

Kosaku Takeda et al.; Blueing of Sepal Colour of *Hydrangea macrophylla*; 84, Phytochemistry, vol. 24, No. 10 pp. 2251–2254; 1985.

Dr. O. Grube et al., "The colour of red cabbage as an indicator in the pH–range 8.5–10", (English Abstract), one page.

K. Takeda et al., "Copigments in the blueing of sepal colour of *Hydrangea macrophylla*," Phytochemistry, vol. 24, No. 6, pp. 1207–1209, 1985.

K. Takeda et al., "Stable blue complexes of anthocyanin–aluminium–3–p–courmaroyl– or 3–caffeoyl–quinic acid involved in the blueing of *Hydrangea* flower," Phytochemistry, vol. 29, No. 4, pp. 1089–1091, 1990.

Jurd and Asen, "The Formation of Metal and "Co–pigment" Complexes of Cyanidin 3–glucosides", Phytochemistry, 5 pp. 1263–71 (1966).

*Primary Examiner*—N. Bhat
(74) *Attorney, Agent, or Firm*—Hunton & Williams LLP

(57) ABSTRACT

A process for modifying the taste and/or odor properties of a food coloring substance having unpleasant taste and/or odor properties is disclosed. There is also provided a process for obtaining a blue non-bleeding color that seems approvable by most health authorities. The invention is useful in food products, sweets and pharmaceutical products ingested orally.

21 Claims, No Drawings

FOOD COLORING SUBSTANCES AND METHOD FOR THEIR PREPARATION

CROSS-REFERENCE TO PRIORITY APPLICATIONS

This application claims the benefit of priority of European patent application EP 01202857.7, filed Jul. 26, 2001 and U.S. application 60/308,108, filed on Jul. 30, 2001, the contents of which are incorporated herein by reference.

BACKGROUND OF THE INVENTION

1. Field of the Invention

The present invention relates to food colouring substances useful, for example in the manufacture of food products, sweets and pharmaceutical products.

2. Background

Colouring substances containing natural or synthetic colouring substances are commonly used in the manufacturing of food products and pharmaceutical products. A wide range of synthetic colouring substances are commercially available making it possible for the manufacturer of food products, sweets and pharmaceutical products, where a particular colour tone is desired, to select a single colouring substance having the desired colour or a mixture of colouring substances, which in appropriate combination impart the desired colour to the product.

Due to consumer pressure there is a trend to replace the synthetic colouring substances with natural ones. However, the use of natural colouring substances implies various problems such as lack of blue colour, acceptable in food substances, unpleasant taste and odour and bleeding, (i.e. diffusion of colour from the food into the environment). These three problems will in the following be presented in more detail and a coherent solution will be disclosed.

Firstly, one problem is that most natural colouring substances used in food products are red, orange or yellow and not blue. There are presently no natural blue colouring substances that are legally approvable for use in foodstuffs marketed in Europe and the USA.

The same problem applies to some extent to green colours. Copper chlorophyll and copper chlorophyllin are efficient and relatively stable green colouring substances but in some countries they are not considered "natural" from a legislation point of view. If a satisfactory natural blue colouring substance could be produced, one might produce a natural green by blending it with a natural yellow colour substance like e.g. turmeric.

It is known from the prior art that some anthocyanins, for example those found in red cabbage leaves, give a blue colour in alkaline solution. Thus, a bright blue colour is normally obtainable at high pHs (almost 8 and above) which is inappropriate for food usage, e.g. Grube, O. et al. "The pigment of red cabbage as an indicator in the pH range 8.5–10.", Chem. Ztg., 67, 34, 1943. However, in this range of pH anthocyanins and other food ingredients are often unstable.

The existence and preparation of blue complexes with aluminium and magnesium from anthocyanins derived from petals and sepals from the flowers of hydrangea and Chinese bellflower is known from the prior art.

Chenery revealed in "The problem of the blue hydrangea" J. Roy. Hort. Soc., 62, 304 (1937) noted that hydrangea hortensis petals would turn blue if its soil was watered with aluminium salts and that aluminium would accumulate in the petals. No such effect on anthocyanins present in or derived from other parts of plants such as e.g. red cabbage leaves or purple carrots was mentioned.

Susumu Maekawa et al. found in "Effect of Aluminium Ions on the bluing of Petal Color in Cut Chinese Bellflower, *Platycodon grandiflorum*", Plant & Cell Physiol. 24(4): 759–764 (1983) that petal colour of Chinese bellflower changed from blue-violet to blue after cut flowers were placed in a solution containing aluminium ions. This was also observed when aluminium ions were added to a solution of anthocyanins extracted from petals from this flower. No such effect on anthocyanins present in or derived from other parts of plants such as e.g. red cabbage leaves or purple carrots was mentioned.

Asen and Siegelman: "Effect of Aluminium on Absorption Spectra of the Anthocyanin and Flavonols from Sepals of *Hydrangea macrophylla* var. *Merveille*", Proc. Am. Soc. Hort. Sci. 70, 478 (1957) found that addition of aluminium to a solution of anthocyanins extracted from *Hydrangea macrophylla* var. *Merveille* could change the colour of the solution from red to blue. No such effect on anthocyanins present in or derived from other parts of plants such as e.g. red cabbage leaves or purple carrots was mentioned.

Kosaku Takeda et al.: "Blueing of sepal colour of *Hydrangea macrophylla*", Petrochemistry, vol. 24, No. 10, pp. 2251–2254, 1985 found that the blue colour of *Hydrangea macrophylla* sepals was mainly due to a blue anthocyanin-aluminium complex.

No reference was made to anthocyanins present in or derived from other parts of plants such as e.g. red cabbage leaves or purple carrots.

EP 0 873 680 A1 describes a method of changing the colours of petals containing anthocyanin in a more bluish direction by the addition of a Lewis acid or aluminium salts, but without mentioning any such effect on anthocyanins present in or derived from other parts of plants such as e.g. red cabbage leaves or purple carrots.

A major difference between the anthocyanins from these flowers and the ones from red cabbage is that the anthocyanins from the flowers mainly consist of delphinidin derivatives and the anthocyanin from red cabbage mainly consists of cyanidin-3-glucosides. (Jurd and Asen (1966), and Takeda et al. (1990)

Jurd & Asen (1966) and Takeda (1990) have published a few in vitro studies on metal, including aluminium, complexes with purified anthocyanins, including cyanidin-3-glucoside.

Jurd and Asen (1966) added quercitrin and chlorogenic acid to solutions of purified cyanidin-3-glucoside and aluminium at pH 5.5. With quercitrin a cerise complex formed. With chlorogenic acid an insoluble, almost blue, extremely insoluble precipitate formed.

Takeda et al. (1990) added 3-p-coumaroylquinic acid to solutions of purified cyanidin-3-glucoside and aluminium at pH 3.7. Increasing levels of 3-p-coumaroylquinic acid gave a more bluish-purple colour hue.

Secondly, another problem by using natural colouring substances for obtaining a blue colour is that extracts containing anthocyanins, especially red cabbage extract, are typically associated with unpleasant tastes and odours when applied in food products, sweets and pharmaceutical products which is a disadvantage Prior art such as Sapers, G M., "Deodorization of a colorant prepared from red cabbage.", J Food Sci., 47, pp. 972–976, 1982 discloses methods for solving this problem through purification steps However, these methods suffer from being insufficient as the unpleasant tastes and odours often develop after the purification of the anthocyanin has been performed In conclusion it has so far been technically impossible to permanently remove the organoleptical problems associated with extracts from vegetables such as red cabbage and purple carrot.

Thirdly, yet an additional problem by using natural colouring substances for obtaining a blue colour, is that as anthocyanins are more or less water soluble, they will leak and "bleed" if in an aqueous environment. This is particular a visible problem if used in a multi-compartment food system where the different compartments have different colours.

The above three problems associated with the use of natural colouring substances have been presented and it is obvious that the problems concentrate mainly on lack of availability of legal and technical requirements.

The preparation of aluminium lakes of dyes is well-described for a lot of dyes, especially synthetic dyes. However, no aluminium lakes of anthocyanins or blue lakes of other natural colouring substances have been described hitherto, that are legally acceptable in food substances.

U.S. Pat. No. 833,602 teaches a laking process involving acid colouring materials and alkaline aluminium salts. However, only lakes of synthetic colouring materials are described.

U.S. Pat. No. 2,053,208 teaches a Taking process for synthetic dyes using aluminium sulphate and sodium aluminate. However, sodium aluminate is not allowed as a process aid for manufacturing of colouring aids for foods according to food legislation in the EU.

W. A. Blumenthal gives in "American Dyestuff Reporter", Nov. 18, 1946, vol. 23, pp 529–545 a review on colour lakes. He mostly deals with lakes of synthetic colours but he also briefly describes lakes of some natural dyes: cochineal, lac-dye, alkermes, Indian yellow, purple snail, logwood, fustet, quercitron, indigo, redwood. None of these lakes based upon natural dyes contain anthocyanins to any significant degree.

U.S. Pat. No. 3,909,284 describes a method of making dry edible non-toxic colour lakes approvable for food and drug use by reacting synthetic colouring substances with sodium hydrogen carbonate and aluminium chloride under very specific conditions. However, only laking with synthetic colouring substances is described.

EP 0 025 637 A1 teaches methods of producing different metal lakes of the natural colouring substance curcumin which is very different from anthocyanins.

U.S. Pat. No. 4,475,919 describes a method of providing lakes of natural colouring substances for foods with starch or cellulose. No aluminium lakes of anthocyanins are mentioned or obvious.

None of the above references disclose any solution or circumvention to firstly the desire of providing natural blue colouring substances that are legally approvable for use in foodstuffs and are blue at normal food pH values, and secondly the market need of providing a lasting removal of the organoleptical problems associated with extracts from vegetables such as e.g. red cabbage and purple carrot.

SUMMARY OF THE INVENTION

According to the present invention, a lasting masking of the unpleasant tastes and odours is obtained, which will be described in detail below.

According to the present invention, a food colour is transformed from being water soluble into being water insoluble, where leaking and bleeding problems are circumvented.

Further, according to the present invention an anthocyanin-aluminium lake is prepared by a procedure, whereby an aluminium containing compound is combined with the food coloring substance, followed by adjustment of the pH to a value of from about 5 to about 9, preferably from 6 to 8, to cause precipitation of the lake.

It has now surprisingly been found by the inventors that the three problems described above can all be solved or circumvented by preparation of an aluminium lake of the natural colouring substances. The aluminium lake may be prepared by combining an aluminium containing compound and the food colouring substance, followed by adjustment of the pH to a value of from about 5 to about 9, preferably from about 6 to about 8, to cause precipitation of the lake.

Also surprisingly, it has been found by the inventors that the desire and need mentioned above can be met by preparation of an aluminium lake of the food colorant. The aluminium lake may be prepared by combining an aluminium containing compound with the food colouring substance, followed by adjustment of the pH to a value of from about 5 to about 9, preferably from about 6 to about 8, to cause precipitation of the lake. These pH ranges include values of from about 5 to about 9 and from about 6 to about 8, respectively, for all embodiments of the invention. In accordance with a preferred embodiment of the invention the food colouring substance comprises anthocyanins originating from other parts of plants than flower petals.

DETAILED DESCRIPTION

In a particularly preferred embodiment, the food colouring substance is an extract of purple carrot or most preferably a red cabbage extract.

In the present context, food colouring substances are interchangeable used with food colorants and is to be understood as substances which may be added to food products, sweets, confectionary, beverages, pharmaceuticals and similar other products to be ingested orally.

Likewise, food products in the present context is to be understood as any edible product comprising nutrients, sweets, confectionary, beverages and pharmaceuticals.

Further, the term aluminium lake denotes herein a type of colouring composition consisting essentially of a colouring substance combined more or less definitely with alumina (or an aluminum containing compound). An aluminium lake is prepared by reacting the colouring substance with alumina (or an aluminum containing compound) under aqueous conditions. The conditions are adjusted in a way that favours precipitation of the coloring composition.

The present invention provides a process for modification of the taste and/or odour properties of a colouring substance for foods, sweets and pharmaceuticals. Surprisingly it has been found by the inventors that this process implies masking of previous unpleasant taste and/or odour properties.

A further aspect of the invention provides a process for producing a food colouring substance (e.g. a food colouring substance), having a blue colour at a pH in the range of from about 5 to about 9, which process comprises treating a food colouring substance which is contains an anthocyanin compound with an aluminium compound, and adjusting the pH to a value of from about 5 to about 9, to produce an aluminium lake comprising the anthocyanin compound.

As said above, according to the present invention an anthocyanin-aluminium lake is prepared by a procedure, whereby an aluminium containing compound is combined with the food colouring substance, followed by adjustment of the pH to a value of from about 5 to about 9, preferably from about 6 to about 8, to cause precipitation of the lake. The pH values of from about 5 to about 9, preferably from about 6 to about 8, include pH values of 5 to 9, preferably 6 to 8, as well as pH values of 5, 6, 8 and 9.

The adjustment of the pH may be done after the colouring substance has been combined with the aluminium compound An example is a process wherein the food colouring substance is combined with a solution or suspension of an aluminium compound, and the pH is then raised to a value of from about 5 to about 9, preferably a pH value from about 6 to about 8 Working examples 1–3 and 8 are examples of such processes.

However, the adjustment of the pH may also be done while combining the colouring substance with the aluminium compound. An example is a process as described herein, wherein the food colouring substance is treated with an aluminium compound under a stably maintained pH value and wherein the stably maintained pH value is a value from pH about 5 to pH about 9. Preferably, the stably maintained pH value is a value from pH 6 to pH 8. Working example 12 provides an example of such a process. The term "stably maintained pH value" means that pH is maintained substantially constant at the specified value.

An advantage of stably maintaining the pH is that, during the precipitation process, a blue free flowing and easily pourable suspension may be formed. This suspension may be used as a suitable colour composition without any need of including a filtration step during the process.

In a preferred embodiment, the product may be encapsulated, using conventional microencapsulation techniques suitable for food products, for example as described in WO 97/26803, for example by encapsulation in gum arabic. The product with or without encapsulation may be used as it is or it may be collected for example by filtration. The filtrate may be dried or used as a wet precipitate without drying.

A further aspect of the invention is a natural colouring substance for foods, sweets and pharmaceuticals, comprising an food colouring substance having unpleasant taste and/or odour properties, combined with an aluminium-containing compound, to form an aluminium lake, wherein the unpleasantness of the taste and/or odour of the colouring material is reduced by said combination with the aluminium-containing compound.

Said food colouring substance characterised by having unpleasant taste and/or odour properties is preferably an anthocyanin, in particular, an anthocyanin of the general formula:

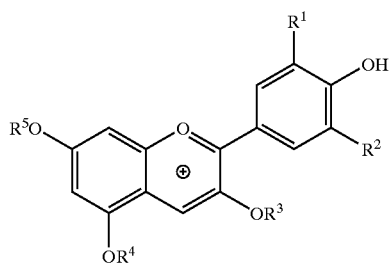

wherein $R^1$ and $R^2$ are each independently H, OH or $OCH_3$, and $R^3$, $R^4$ and $R^5$ are each independently H, a sugar residue or an acylated sugar residue. The sugar residues are most commonly residues derived from glucose, galactose, xylose, arabinose and rhamnose; substitution with disaccharides also occurs e.g. rutinose, sophorose, sambubiose, and gentiobiose. These residues are examples only and are not to be understood as a complete list.

A particularly advantageous feature of the anthocyanin-based products of the present invention is that the blue colour of the anthocyanin colourant is retained at pHs of about 8 or less, for example at pHs in the range about 6 to about 8.

A number of preferred embodiments of the invention is described in the following examples:

In the examples 1, 2, 3 and 8 below, spray dried red cabbage or purple carrot extracts, were used, which were diluted with maltodextrine to give a standardised "colour content", expressed in Colour Units.

The colour content is measured as follows:

P grams of the standardised spray dried extract are dissolved in 100 ml 0.1 M citrate-HCl buffer at pH 3.0. This solution should have a concentration such as to give an optical density in the range of from 0.5 to 1.0 (with a distilled water blank).

Colour content measured in Colour Units is defined by the formula:

$$\text{Optical density(OD) at lambda max*/P (grams)}$$

*lambda max=wavelength between 500 nm and 550 nm giving the highest OD value.

Other inert materials like sugars and salts could have been used as well for standardisation of the spray dried extracts without any significant changes of the results obtained below. In examples 4, 5, 6 and 7 a red cabbage extract was used, that was standardised to a colour content of 15.8 Colour Units per gram with deionised water.

In all examples where aluminium sulphate was applied the compound with 18 moles of water of crystallization per mole (Merck Aluminiumsulfat-18-hydrat, Stücke reinst, Ph Eur, BP) was used.

In all examples where aluminium chloride was applied the compound with six moles of water of crystallisation was used (CG Chemikalien Aluminiumchlorid-6-hydrat, Ph. Eur., BP, USP).

EXAMPLE 1

This Example Discloses an Example of Preparation of Blue Al-anthocyanin Lakes with Spray-Dried Red Cabbage Extract, Ratio Aluminium Sulfate:Red Cabbage Extract=2:1

An amount of 10 grams of a spray-dried red cabbage extract, standardised with maltodextrine to a colour content of 30 Colour units per gram, were dissolved in 100 ml of demineralised water. 20 grams of aluminium sulphate were dissolved in 100 mL of demineralised water. The two solutions were mixed. The pH of the mixed solution was 3.0. pH was raised to 7.9 by the addition of 5% ammonia (J. Baker, Ammonium Hydroxide 25%). A blue precipitate was formed, and was collected by vacuum filtration. The filtrate was only weakly coloured (greenish), indicating almost complete laking of the colour. The blue precipitate was dried overnight at 40 degrees C.

EXAMPLE 2

This Example Discloses an Example of Preparation of Blue Al-anthocyanin Lakes with Spray-Dried Red Cabbage Extract, Ratio Aluminium Sulfate:Red Cabbage Extract=1:1

An amount of 4 grams of a spray dried red cabbage extract, standardised with maltodextrine to a colour content of 30 Colour units per gram, were dissolved in 180 ml of demineralised water. An amount of 4 grams of aluminium sulphate were dissolved in 20 mL of demineralised water.

The two solutions were mixed. The pH of the mixed solution was 3.0. pH was raised to 7.9 by the addition of 5% ammonia (J. Baker, Ammonium Hydroxide 25%). The blue precipitate was collected by vacuum filtration. The filtrate was strongly coloured (blue), indicating incomplete laking of the colour. The blue precipitate was dried overnight at 40 degrees C.

EXAMPLE 3

This Example Discloses an Example of Preparation of a Blue Al-anthocyanin Lakes with Spray-Dried Red Cabbage Extract, Ratio Aluminium Sulfate:Red Cabbage Extract=3:1

An amount of 10 grams of a spray dried red cabbage extract, standardised with maltodextrine to a colour content of 30 Colour units per gram, were dissolved in 100 ml of demineralised water. An amount of 30 grams of aluminium sulphate were dissolved in 100 mL of demineralised water. The two solutions were mixed. The pH of the mixed solution was 3.0. pH was raised to 7.9 by the addition of 5% ammonia (J. Baker, Ammonium Hydroxide 25%). The blue precipitate was collected by vacuum filtration. The filtrate was only weakly coloured (greenish), indicating almost complete laking of the colour. The blue precipitate was dried overnight at 40 degrees C.

EXAMPLE 4

This Example Demonstrates a Method for Preparation of Microencapsulated Blue Al-anthocyanin Lakes with Red Cabbage Extract An amount of 145,2 g red cabbage extract was added to 300 g of sugar syrup (Hvid Sirup, Danisco) and 300 g dem. water, 150 g aluminium sulphate and 150,0 g gum Arabic (Instant Soluble Gum Arabic, Alland & Robert) were added and left to dissolve. After dissolution pH was measured to be 1,7 and the temperature was measured to be 42 degrees C. pH was increased to 7,5 by the addition of 113,1 g of a solution (J. Baker, Ammonium Hydroxide 25%) of ammonia in water. 144,4 g dem. water was added. The suspension was milled in a Dynomill type KDL ball mill, as described in patent application WO 97/26803. A beadlet size of 0,6–0,8 mm was applied in the mill. The suspension was allowed to pass the mill three times. The milled suspension was characterized in a Malvern Mastersizer. The mean particle diameter of the colour lake particles was 0.48 micrometer after the milling.

To 700 g of the milled suspension 124 g of propylene glycol (Lyondell, France) was added.

EXAMPLE 5

This Example Provides an Example of a Procedure for Comparison of the Organoleptical Properties of Microencapsulated Lakes with those of Untreated Red Cabbage Extract, when Applied in Sweets The microencapsulated preparation produced according to Example 4 was compared to a standard red cabbage extract in a panning test where chocolate pastilles were coated with coloured sugar syrups as follows:

Materials and Methods:

A sugar syrup was made of 444 g sucrose, 200 g dem. water and 13 g of glucose syrup (DE 42, 80% glucose). An amount of 300 grams of chocolate pastilles were coated in each trial. In the first trial a syrup containing 8% of the microencapsulated preparation produced according to example 4, was used for the coating. A total of 47.7 grams of coloured syrup was applied. In the second trial a syrup containing 2% of the red cabbage extract used in example 4 and adjusted to pH 7.5 was used. A total of 34.2 grams of coloured syrup was applied.

Results of Characterisation of Colour:

The coated pastilles produced using the microencapsulated preparation according to Example 4 had a blue colour (similar to Royal Horticultural Society colour chart 92 B) while the ones coated with the red cabbage extract had a purple colour (similar to Royal. Horticultural Society colour chart 98 B)

Results of Characterisation of Taste:

The coated pastilles produced using the microencapsulated preparation according to Example 4 did not have any "cabbage taste" whereas the ones coated with the red cabbage extract had a strong "cabbage taste".

It appears clearly that the use of the microencapsulated lakes according to the invention renders a more bluish colour hue and a masking of the unpleasant "cabbage taste".

EXAMPLE 6

This Example Provides a Comparison of Colour Hues of Microencapsulated Lakes with those of Untreated Red Cabbage Extract at Different pH-values The microencapsulated preparation produced according to example 4 was compared to red cabbage extract in water-sugar blends (fondants) at different concentration levels and pH values. Two different concentration levels were measured at four different pH-values with regard to colour hue and visual appearance.

Buffer solutions were prepared from 0.1 M NaOH and 0.1 M $KH_2PO_4$ solutions. Both microencapsulated preparation produced, according to Example 4, and red cabbage extract were tested in two concentration levels at pH 6.5, 7.0, 7.5 and 8.0. pHs were measured after mixing of colour solutions and buffer solutions. For red cabbage extract two levels were tested: 0.10 grams and 0.50 grams of extract per 25 ml of colour solution which in tables 1 and 3 is stated as low concentration level and high concentration levels, respectively. For the microencapsulated preparation produced according to Example 4, two levels were tested: 1.07 grams and 5.35 grams per 25 ml of colour solution which in tables 2 and 4 is stated as low concentration level and high concentration levels, respectively.

Fondants were prepared from 10 mL colour solution and 50 grams of icing sugar (Danisco), which were intensively mixed.

The colours of the coloured fondants were characterized in a Minolta 300 colour tester. The Minolta characterises the colour shade by measuring the hue angle, measured in degrees, where pure red: 360, pure yellow: 90, pure green: 180, pure blue: 270). Purple shades will have values between 360 and 270, the more bluish, the closer to 270.

Results

TABLE 1

| red cabbage extract, low concentration level | | | | |
|---|---|---|---|---|
| pH of colour solution | 6.5 | 7 | 7.5 | 7.9 |
| Colour hue of sugar fondant, measured on Minolta 300 | 314.3 | 305.6 | 293.7 | 283.8 |
| Visual appearance | purple | bluish purple | bluish purple | blue |

TABLE 2

| microencapsulated preparation produced according to Example 4, low concentration level | | | | |
|---|---|---|---|---|
| pH of colour solution | 6.5 | 7.1 | 7.7 | 8.1 |
| Colour hue of sugar | 278.7 | 271.5 | 263.6 | 259.4 |

TABLE 2-continued microencapsulated preparation produced according to Example 4, low concentration level

| fondant, measured on Minolta 300 | | | | |
|---|---|---|---|---|
| Visual appearance | bluish purple | blue | blue | blue |

TABLE 3 red cabbage extract, high concentration level

| pH of colour solution | 6.4 | 6.9 | 7.6 | 8.2 |
|---|---|---|---|---|
| Colour hue of sugar fondant, measured on Minolta 300 | 323.0 | 317.4 | 310.2 | 302.6 |
| Visual appearance | purple | purple | bluish purple | blue |

TABLE 4 microencapsulated preparation produced according to Example 4, high concentration level

| pH of colour solution | 6.6 | 7.1 | 7.6 | 8 |
|---|---|---|---|---|
| Colour hue of sugar fondant, measured on Minolta 300 | 276 | 276.7 | 270 | 265.1 |
| Visual appearance | blue | blue | blue | blue |

By comparison of Table 1 with Table 2 and Table 3 with Table 4 it appears that for the same pH-value a more bluish colour hue is obtained by using the microencapsulated colour lake according to the invention than obtained with the untreated cabbage extract.

EXAMPLE 7

This Example provides a Comparison of Colour Hues of Microencapsulated lakes with those of Untreated Red Cabbage Extract at Different pH-values The microencapsulated preparation produced according to Example 4 was compared to a standard red cabbage extract in water-sugar blends (fondants) at different levels and pHs in stronger buffer solutions.

Materials and Methods:

Buffer solutions were prepared from 1.0 M NaOH and 1.0 M $KH_2PO_4$ solutions. Both microencapsulated preparations produced according to Example 4 and red cabbage extract were tested in two concentration levels at pH 8.5, 7.0, 6.5 and 6.0.

pHs were measured after mixing of colour solutions and buffer solutions. For red cabbage extract two concentration levels were tested: 0.10 gram and 0.50 gram of extract per 25 ml of colour solution as described in Example 6. The two concentration levels are designated low and high in tables 1 and 3 below. For the microencapsulated preparation produced according to example 4 the following two levels were tested: 1.07 grams and 5.35 grams per 25 ml of colour solution, which were designated low and high concentration level, respectively.

Fondants were prepared as described in Example 6.

The colours of the coloured fondants were characterised in a Minolta 300 as described in Example 6.

Results:

TABLE 1 red cabbage extract, low concentration level

| pH of colour solution | 6.0 | 6.5 | 7.0 | 8.5 |
|---|---|---|---|---|
| Colour hue of sugar fondant, measured on Minolta 300 | 317.5 | 309.6 | 292.8 | 251.7 |
| Visual appearance | purple | purple | bluish purple | blue |

TABLE 2 microencapsulated preparation produced according to Example 4, low concentration level

| pH of colour solution | 6.0 | 6.5 | 7.0 | 8.5 |
|---|---|---|---|---|
| Colour hue of sugar fondant, measured on Minolta 300 | 314.4 | 293.4 | 271.0 | 244.2 |
| Visual appearance | purple | bluish purple | blue | blue |

TABLE 3 red cabbage extract, high concentration level

| pH of colour solution | 6.0 | 6.5 | 7.0 | 8.5 |
|---|---|---|---|---|
| Colour hue of sugar fondant, measured on Minolta 300 | 318.6 | 310.0 | 300.5 | 279.9 |
| Visual appearance | purple | purple | bluish purple | blue |

TABLE 4 microencapsulated preparation produced according to Example 4, high concentration level

| pH of colour solution | 6.0 | 6.5 | 7.0 | 8.5 |
|---|---|---|---|---|
| Colour hue of sugar fondant, measured on Minolta 300 | 296.5 | 296.6 | 257.3 | 229.7 |
| Visual appearance | bluish purple | bluish purple | blue | blue |

By comparison of Table 1 with Table 2 and Table 3 with Table 4 it appears that for the same pH-value a more bluish colour hue is obtained by using the microencapsulated colour lake according to the invention than obtained with the untreated cabbage extract.

EXAMPLE 8

This Example Discloses an Example of Preparation of Blue Al-anthocyanin Lakes with Spray-Dried Purple Carrot Extract Preparation of Solution 1:

Solution 1 was prepared by dissolving 10 grams of a spray dried purple carrot extract, standardised with maltodextrin to a colour content of 12 Colour units per gram, in 100 ml of demineralised water.

Preparation of Solution 2:

Solution 2 was prepared by dissolving 20 grams of aluminium sulphate in 100 mL of de-mineralised water.

Solutions 1 and 2 were mixed. The pH of the mixed solution was measured to be 3.0. pH was raised to 7.9 by the addition of 5% ammonia (J. Baker, Ammonium Hydroxide 25%). A blue precipitate was formed, and it was collected by vacuum filtration. The filtrate was only weakly coloured (greenish), indicating almost complete laking of the colour. The blue precipitate was dried overnight at 40 degrees C.

EXAMPLE 9
This Example Discloses the Result of the Lake Preparation Method Described in Examples 1, 2, 3 and 8 when Applied to Spray-Dried Sweet Potato Extract.

An amount of 33 grams of a spray dried sweet potato extract, standardised with maltodextrin to a colour content of 3,2 Colour units per gram, and 20 grams of aluminium sulphate were dissolved in 300 mL of demineralised water. The pH of the mixed solution was 2.0. The colour of the solution was red. pH was raised to 7.9 by the addition of 5% ammonia (J. Baker, Ammonium Hydroxide 25%). However, the colour remained red and no precipitate formed.

EXAMPLE 10
Black Currant Extract

An amount of 20 grams of a spray dried blackcurrant extract, standardised with maltodextrin to a colour content of 6.82 Colour units per gram, and 10 grams of aluminium sulphate were dissolved in 300 mL of demineralised water. The pH of the mixed solution was 3.0. The colour of the solution was red. pH was raised to 7.9 by the addition of 5% ammonia (J. Baker, Ammonium Hydroxide 25%). A blackish-blue precipitate formed.

EXAMPLE 11
Elderberry Extract

An amount of 33 grams of a spray dried elderberry extract, standardised with maltodextrin to a colour content of 4.17 Colour units per gram, and 10 grams of aluminium sulphate were dissolved in 300 mL of demineralised water. The pH of the mixed solution was 2.2. The colour of the solution was red. pH was raised to 8.0 by the addition of 5% ammonia (J. Baker, Ammonium Hydroxide 25%). A blackish-blue colour but almost no precipitate formed.

EXAMPLE 12
This Example Discloses the Results of Lake Preparation Using Aluminium Chloride, Using Precipitation at Constant pH and Without the Filtration Step A solution was prepared of 200 grams of a spray dried red cabbage extract, standardised with maltodextrin to a colour content of 30 Colour units per gram, 250 grams of demineralised water and 50 grams of propylene glycol. 444,4 grams of this solution was put into an automatic titrator where pH set point was 6,5. 88,88 grams of solid Aluminium chloride was slowly added to the solution while the pH was kept at 6,5 with 20% solution of sodium hydroxide in demineralised water.

During the precipitation process the reaction chamber was stirred with a Silverson Batch Mixer. A deep blue, free flowing and easily pourable suspension was obtained. The colour strength of the suspension was 5,66 Colour units per gram. The particle size distribution was measured in a Malvern Mastersizer and the mean diameter found to be 1,50 microns. The colour strength was adjusted to 5,0 Colour units per gram using solid sodium chloride.

EXAMPLE 13
This Example Provides a Procedure for Comparison of the Colour Intensity and Taste of Sweets where Lakes had been Used for Colouring Compared with Sweets where Untreated Red Cabbage Extract had been Used A sugar syrup was made of 444 g sucrose, 200 g dem. water and 13 g of glucose syrup (DE 42, 80% glucose). Two trials were made and 300 g of chocolate pastils were coated in each. In trial 1 a syrup containing 4% of a colour suspension prepared according to example 12 was used for coating. This gave a colour strength of 0,2 CU/g in the coloured syrup. pH of the coloured syrup was 6,4 and the colour was bright blue. A total of 39,9 g grams of the coloured syrup was applied for coating. In trial 2 a 40% solution of a spray dried red cabbage extract, standardised with maltodextrin to a colour content of 30 Colour units per gram, was prepared. 1,66% of this solution was added to the sugar syrup. Before pH adjustment the pH of the solution was 6,5 and the colour was purple. pH in the coloured syrup was then adjusted to 7,7 with 20% NaOH in order to obtain the same bright blue colour as that of the aluminium lake. After the pH adjustment the coloured syrup had a colour strength of 0,2 CU/g. A total of 41,5 grams of this syrup was then applied for coating.

Results

|  | Trial 1: 39.6 g of lake suspension applied | Trial 2: 41.5 g of red cabbage solution at pH 7.7 applied |
|---|---|---|
| Taste | no cabbage taste | cabbage taste |
| Colour intensity | intense dark blue colour | lighter blue colour |

These results clearly demonstrate that a more intense colour and a better taste is obtained with the colour lake than with the same amount of colour used as untreated red cabbage extract

EXAMPLE 14
This Example Provides a Comparison of the Colour Intensity and Colour Hue of Lakes Compared with those of Untreated Red Cabbage Extract, when Applied in Sugar Syrup A sugar syrup just like those used for panning of confectionary was prepared by mixing 68% sucrose, 30% demineralised water and 2% maltodextrin and boiling until all solids had dissolved. Coloured syrups were made by adding either 0,06% of a product produced according to the description in example 12 (5,0 CU/g) or a solution containing 5,0 CU/g of spray dried red cabbage extract. Coloured sugar syrups with pH's from about 1.5 to 9.0 were then prepared by adding sodium hydroxide or hydrochloric acid. The coloured syrups where then characterised in a Minolta CT 310 and chroma, hue angle and L-values of the syrups were plotted as functions of pH. The results are given below:

| Chroma and hue angle as a function of pH in syrup, colour lake | | |
|---|---|---|
| pH | Hue (degrees) | Chroma |
| 1.5 | 314 | 30.0 |
| 2.6 | 294 | 21.4 |
| 3.1 | 285 | 19.8 |
| 3.4 | 281 | 19.0 |
| 3.9 | 275 | 18.4 |
| 4.9 | 267 | 18.0 |
| 5.5 | 264 | 18.2 |
| 6.2 | 258 | 18.4 |
| 6.5 | 254 | 18.5 |
| 7.4 | 249 | 18.7 |
| 7.7 | 246 | 18.6 |
| 8.1 | 243 | 18.5 |

-continued

Chroma and hue angle as a function of pH in syrup, colour lake

| pH | Hue (degrees) | Chroma |
|---|---|---|
| 8.5 | 239 | 18.1 |
| 8.8 | 234 | 17.8 |

Chroma and hue angle as a function of pH in syrup, red cabbage extract

| pH | Hue (degrees) | Chroma |
|---|---|---|
| 1.7 | 350 | 41.2 |
| 2.3 | 349 | 37.5 |
| 3.0 | 346 | 32.0 |
| 3.6 | 341 | 24.8 |
| 4.4 | 332 | 17.0 |
| 5.4 | 322 | 13.5 |
| 5.8 | 311 | 12.2 |
| 6.1 | 316 | 14.4 |
| 6.2 | 309 | 12.5 |
| 6.6 | 301 | 12.2 |
| 7.3 | 277 | 12.4 |
| 7.6 | 263 | 13.8 |
| 7.9 | 249 | 14.9 |
| 8.3 | 237 | 15.8 |
| 8.7 | 228 | 16.6 |

The results clearly demonstrate that the syrups which have been coloured with the compositions according to the invention the following advantages have been obtained when compared to the syrups coloured with untreated red cabbage extracts:

a more bluish colour hue for all pH's of relevance to foods: 2–8 a more pH independent, constant colour intensity (chroma)

a higher colour intensity (chroma) at pH's found in most foods: 4–8

Reference

Asen and Siegelman: "Effect of Aluminium on Absorption Spectra of the Anthocyanin and Flavonols from Sepals of *Hydrangea macrophylla* var. *Merveille*", Proc. Am. Soc. Hort. Sci. 70, 478 (1957)

Chenery: "The problem of the blue hydrangea", J. Roy. Hort. Soc., 62, pp. 304–320 (1937)

EP 0 025 637, General Foods Corporation, May 23, 1984

EP 0 873 680, Hofstede, Wilhelmus Johannes

Grube, 0. et al. "The pigment of red cabbage as an indicator in the pH range 8.5–10.", Chem. Ztg., 67, 34, 1943

Jurd and Asen, "The formation of Metal and "Co-pigment" Complexes of Cyanidin 3-glucosides", Phytochemistry, 5 pp. 1263–71 (1966)

Kosaku Takeda et al. "Blueing of sepal colour of *Hydrangea macrophylla*", Phytochemistry, vol. 24, No. 10 pp. 2251–2254, 1985

Kosaku Takeda et al., "Stable Blue Complexes of Anthocyanin-Aluminium-3-p-Coumaroyl- Or 3-Caffeoyl-Quinic Acid Involved In The Blueing of *Hydrangea* Flower, Phytochemistry, vol. 29, No. 4, pp. 1089–1091 1990

Sapers, G M "Deodorization of a colorant prepared from red cabbage.", J. Food Sci., 47, 972–976, 1982

Susumu Maekawa et al. found in "Effect of Aluminium Ions on the bluing of Petal Color in Cut Chinese Bellflower, *Platycodon grandiflorum*", Plant & Cell Physiol. 24(4): 759–764 (1983)

U.S. Pat. No. 2,053,208, Merrimac Chemical Company, Sep. 1, 1936

U.S. Pat. No. 3,909,284, Colorcon, Inc., Sep. 30, 1975

U.S. Pat. No. 4,475,919, Colorcon, Inc., Oct. 9, 1984

U.S. Pat. No. 8,33,602, Badische Anilin & Soda Fabrik, Oct. 6, 1906

W. A. Blumenthal "A review of the Literature on Color Lakes", American Dyestuff Reporter, vol. 35, pp 529–545 (1946)

WO 97/26803, Chr. Hansen A/S, Jul. 31, 1997

What is claimed is:

1. A process for modifying the taste and/or odour properties of a food colouring substance having unpleasant taste and/or odour properties, which process comprises treating the food colouring substances, which includes an anthocyanin compounds with an aluminium compound, and adjusting the pH to a value of from about 5 to about 9, to produce an aluminium lake comprising said food colouring substance and said anthocyanin compound wherein the taste and/or odour properties of the lake are organoleptically masked in comparison with those of said food colouring substance.

2. A process as claimed in claim 1, wherein the anthocyanin compound has the formula:

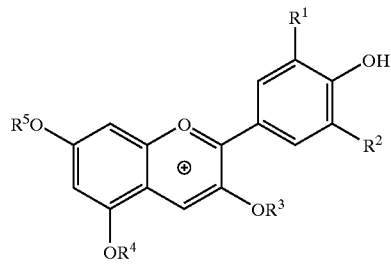

wherein $R^1$ and $R^2$ are each independently H, OH or $OCH_3$, and $R^3$, $R^4$ and $R^5$ are each independently H, a sugar residue or an acylated sugar residue.

3. A process for producing a food colouring substance, having a blue colour at a pH in the range of from about 5 to about 9, which process comprises treating a food colouring substance which is an anthocyanin compound of the formula:

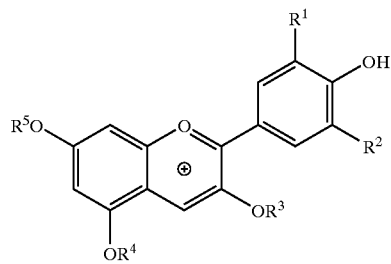

wherein $R^1$ and $R^2$ are each independently H, OH or $OCH_3$, and $R^3$, $R^4$ and $R^5$ are each independently H, a sugar residue or an acylated sugar residue with an aluminium compound, and adjusting the pH to a value of from about 5 to about 9, to produce an aluminium lake comprising the anthocyanin compound.

4. A process as claimed in claim 3, wherein the anthocyanin compound originates from plant parts other than petals or sepals.

5. A process as claimed in any one of the preceding claims, wherein the food colouring substance is an extract of red cabbage or purple carrot.

6. A process as claimed in any of claims 1–4, wherein the food colouring substance is treated with an aluminium compound under a stably maintained pH value and wherein the stably maintained pH value is a value from pH about 5 to pH about 9.

7. A process as claimed in claim 6, wherein the pH value is a value from pH 6 to pH 8.

8. A process as claimed in any of the claims 1 to 4, in which the food colouring substance is combined with a solution or suspension of an aluminium compound, and the pH is then raised to a value of from about 5 to about 9.

9. A process as claimed in claim 8, wherein the pH is raised to a value of from about 6 to about 8.

10. A process as claimed in any of claims 1–4, in which the aluminium compound is aluminium sulphate.

11. A process as claimed in any of claims 1–4, further including a step of micro encapsulating the aluminium lake.

12. A process as claimed in any of claims 1–4, including a step of filtering the aluminium lake.

13. A process as claimed in any of claims 1–4, further including a step of drying the aluminium lake.

14. A colouring composition, comprising a food colouring substance which includes an anthocyanin, the food colouring substance having unpleasant taste and/or odour properties, which food colouring substance is combined with an aluminium-containing compound, to form an aluminium lake, wherein the unpleasantness of the taste and/or odour of the food colouring substance is masked by said combination of the food colouring substance with the aluminium-containing compound.

15. A composition as claimed in claim 14, wherein the food colouring substance is an anthocyanin compound of formula:

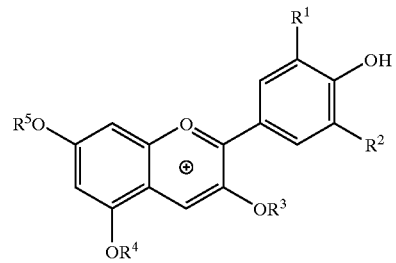

wherein $R^1$ and $R^2$ are each independently H, OH or $OCH_3$, and $R^3$, $R^4$ and $R^5$ are each independently H, a sugar residue or an acylated sugar residue.

16. A food colouring composition, having a blue colour at a pH in the range of from about 5 to about 9, which comprises a food colouring substance which is an anthocyanin compound of formula:

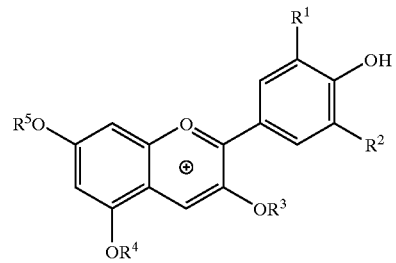

wherein $R^1$ and $R^2$ are each independently H, OH or $OCH_3$, and $R^3$, $R^4$ and $R^5$ are each independently H, a sugar residue or an acylated sugar residue, combined with an aluminium compound to produce an aluminium lake.

17. A composition as claimed in any one of claims 14 to 16, wherein the food colouring substance comprises an extract of red cabbage or purple carrot.

18. A composition as claimed in any one of claims 14 to 16, wherein the composition has a blue colour at a pH in the range of about 6 to about 8.

19. A method of modifying a food product comprising adding to the food product a composition as claimed in any of claims 14–16.

20. A method as claimed in claim 19 wherein the food product includes sweets, confectionary, or a combination of sweets and confectionary.

21. A method as claimed in claim 19 wherein the food product includes a pharmaceutical product.

* * * * *